United States Patent [19]
Suding et al.

[11] Patent Number: 5,480,432
[45] Date of Patent: Jan. 2, 1996

[54] EXTENDED DWELL VOICE PROSTHESIS

[75] Inventors: David R. Suding; Edmund V. Seder, both of Santa Barbara, Calif.

[73] Assignee: Helix Medical Corporation, Carpinteria, Calif.

[21] Appl. No.: 282,277

[22] Filed: Jul. 27, 1994

[51] Int. Cl.$^6$ ................................. A61F 2/20; A61B 1/00
[52] U.S. Cl. ........................... 623/9; 623/11; 128/207.16
[58] Field of Search ......................... 623/9–11; 606/196; 128/207.16, 207.29, 654; 600/23–25

[56] References Cited

U.S. PATENT DOCUMENTS

| | | | |
|---|---|---|---|
| 4,435,853 | 3/1984 | Blom et al. | 3/1.3 |
| 4,572,162 | 2/1986 | Livesay et al. | 128/654 |
| 4,586,931 | 5/1986 | Blom et al. | 623/9 |
| 4,596,579 | 6/1986 | Pruitt | 623/9 |
| 4,614,516 | 9/1986 | Blom et al. | 623/9 |
| 4,773,412 | 9/1988 | Blom | 128/207.14 |
| 4,787,391 | 11/1988 | Elefteriades | 128/654 |
| 4,820,304 | 4/1989 | Depel et al. | 623/9 |
| 4,863,470 | 9/1989 | Carter | 623/8 |
| 4,883,490 | 11/1989 | Oh | 623/22 |
| 4,911,716 | 3/1990 | Blom et al. | 623/9 |
| 5,024,232 | 6/1991 | Smid et al. | 128/654 |
| 5,047,050 | 9/1991 | Arpesani | 623/1 |
| 5,064,433 | 11/1991 | Blom et al. | 623/9 |
| 5,078,743 | 1/1992 | Mikalov et al. | 623/9 |
| 5,139,505 | 8/1992 | Palmieri | 606/154 |
| 5,154,179 | 10/1992 | Ratner | 128/653.4 |
| 5,201,880 | 4/1993 | Wright et al. | 623/2 |
| 5,266,669 | 11/1993 | Onwunka et al. | 528/28 |
| 5,300,119 | 4/1994 | Blom | 623/11 |
| 5,314,470 | 5/1994 | Persson | 623/9 |
| 5,368,027 | 11/1994 | Lübbers et al. | 128/633 |

*Primary Examiner*—David Isabella
*Assistant Examiner*—Laura Fossum
*Attorney, Agent, or Firm*—Marvin E. Jacobs

[57] ABSTRACT

The position of the rear esophageal flange of a voice prosthesis disposed in a tracheoesophageal fistula is determined by forming a distinctive radiopaque pattern on the flange, preferably by insert molding a radiopaque ring along the perimeter of the flange and radiographically imaging the flange to determine the pattern of the ring. Pattern recognition of the ring is improved by forming the concentric flapper valve of radiopaque material.

11 Claims, 3 Drawing Sheets

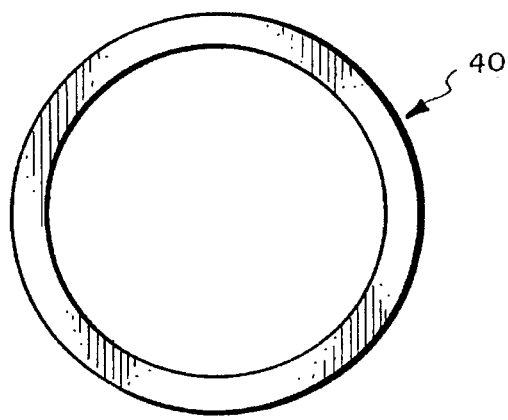
Fig. 6.
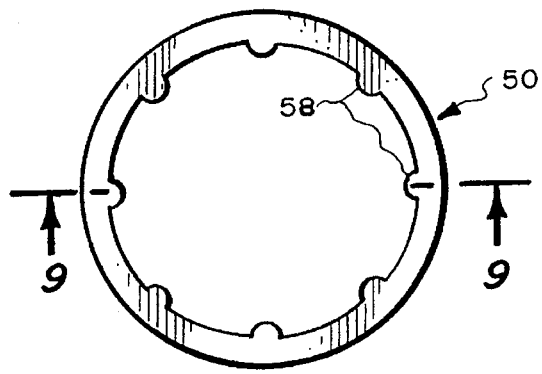
Fig. 8.
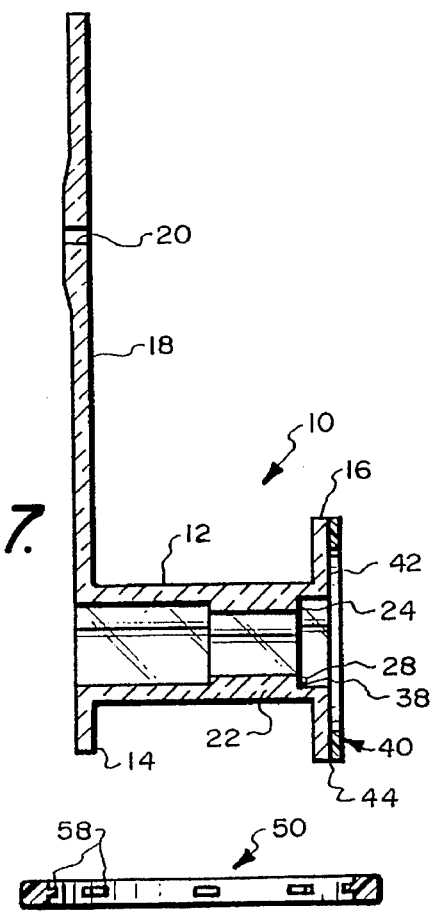
Fig. 7.
Fig. 9.
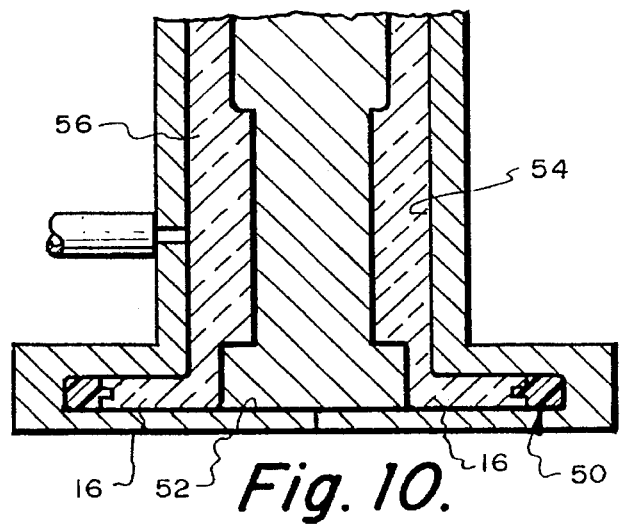
Fig. 10.

5,480,432

EXTENDED DWELL VOICE PROSTHESIS

TECHNICAL FIELD

This invention relates to a voice prosthesis and more particularly this invention relates to a type of voice prosthesis developed for patients who can not themselves insert the voice prosthesis such as quadriplegic patients or patients suffering from neurological conditions such as M.S. The voice prosthesis must be inserted by a health care professional.

BACKGROUND OF THE INVENTION

There are several options for restoring speech to patients who have had their larynx removed. One procedure is to surgically create a puncture or fistula between the trachea and the esophagus. A trachea voice prosthesis containing a one-way valve such as a BLOM-SINGER® voice prosthesis is inserted into the tracheoesophageal fistula. The one-way valve protects the airway during swallowing but opens under positive pressure. The voice prosthesis, thus, permits a patient to divert air from the lungs into the esophagus and out through the mouth. Speech is created during passage of air through the upper part of the esophagus.

The prosthesis maintains the fistula open, transfers air from the trachea to the esophagus for voice production and prevents esophageal leakage into the trachea during swallowing. However, the prosthesis being in contact with moisture in a hot, dark environment is subject to growth of commonly found yeast formation, typically *Candida albicans* on the valve and the retaining flange. The growth of yeast can interfere with function of the valve and can cause the flange to wrinkle and leak.

The current low pressure voice prosthesis can be removed by the patient every few days and can be replaced with a clean prosthesis. The removed prosthesis is soaked in hydrogen peroxide to remove the layer of yeast from the valve and flange. Some patients however, have difficulty managing frequent removal and reinsertion of the prosthesis. Others, who are physically handicapped are not able to remove, sterilize, or reinsert the prosthesis.

| List of References | |
|---|---|
| 4,435,853 | Blom, et al. |
| 4,586,931 | Blom, et al. |
| 4,596,579 | Pruitt |
| 4,614,516 | Blom, et al. |
| 4,773,412 | Blom |
| 4,911,716 | Blom, et al. |
| 5,064,433 | Blom, et al. |
| 5,300,119 | Blom |

STATEMENT OF THE INVENTION

A longer dwelling, low pressure voice prosthesis has been provided in accordance with the invention. The voice prosthesis can remain in place in the tracheoesophageal fistula for over 3–4 days, depending on the patient and conditions of use. The patient can confidently use the prosthesis for longer periods. Trips to a health care specialist to remove and replace the prosthesis are greatly extended providing increased comfort and lower cost to the patient.

The flange or collar that rests against the tracheoesophageal wall is strengthened by increasing the thickness and/or diameter of the flange. The stronger flange is more resistant to wrinkling or detachment from the wall. The voice prosthesis can remain in place in the fistula for much longer periods without allowing leakage between the trachea and the esophagus. The stronger and larger collar also reduces possibility of dislodgment of the prosthesis during a coughing or sneezing episode.

However, the thicker and wider flange is more difficult to insert though the fistula and does not reliably seat on the tracheoesophageal wall. An insertion system as disclosed in U.S. Pat. No. 5,300,119, the disclosure of which is incorporated herein by reference, can be utilized to insert the long dwelling voice prosthesis into the fistula. The thicker flange is folded toward the axis of the tube of the prosthesis and inserted into a gelatin capsule, which is inserted through the fistula. Moisture in the esophagus dissolves the capsule which releases the folded flange which is intended to deploy and seat against the tracheoesophageal wall.

Seating of the retention collar against the anterior wall of the esophagus can be confirmed by rotating the inserted prosthesis within the puncture. Correctly and securely inserted prosthesis will rotate freely, repeatedly through 360°. If the prosthesis does not rotate freely, it suggests that the retention collar has not unfurled and seated. The flange does not fully open and seat in every instance. The body of the prosthesis may be too short or a portion of the flange may be caught in the fistula.

Yeast growth on the valve can also cause distortion of the shape of the valve or form wrinkles in the body of the valve which prevents the valve from closing.

Radiographic assessment is recommended for direct confirmation that the prosthesis retention collar is correctly positioned. It was attempted to provide radiographic assessment by adding a sufficient amount of a radiopaque agent such as barium sulfate to the silicone resin used to manufacture the long-dwelling voice prosthesis. However, since the collar was completely radiopaque, folds in the collar could not be reliably discerned.

A voice prosthesis with a readily visualized retention collar was produced in accordance with the invention by forming the body of the prosthesis with a resin essentially transparent to radiation while applying a distinctive geometric pattern of radiopaque material to the collar. The geometric shape of the pattern is preferably a polygon with uniform sides such as hexagon or a circle. The segments of the polygon can be tangent to the outer edge of the collar. If the collar is folded or twisted, the polygon will not be symmetrical which is readily visualized by X-rays.

The radiopaque pattern such as an annular ring is preferably preformed and applied to a surface of the collar. Another feature of the invention is to place the preformed radiopaque ring in the cavity for molding the voice prosthesis and to embed the ring into the collar during molding. Adherence of the ring to the collar is improved by providing protuberances on a surface of the ring.

The valve is preferably formed with an arcuate dome shape instead of a flat shape. The dome shaped valve has much high resistance to folding or bending. A score line can be provided above the pin connection to act as a live hinge to reduce fatigue on the valve element. The valve can also be formed from a high radiopaque resin composition. The pin connection can fail and the valve can fall into the stomach. The radiopaque valve can be readily located and removed from the stomach. Furthermore, the opaque cylindrical disc image of the valve serves as a reference and locating image for the opaque ring on the collar and also serves as a circular comparison shape to determine whether the collar with the circular opaque ring is fully deployed.

BRIEF DESCRIPTION OF THE DRAWINGS

FIG. 6 is a top view in elevation of a first embodiment of an opaque ring;

FIG. 7 is a partial side view in section showing the ring of FIG. 6 adhesively attached to the esophageal flange of a voice prosthesis;

FIG. 8 is a top view in elevation of another embodiment of an opaque ring;

FIG. 9 is a view in section taken along line 9—9 of FIG. 8;

FIG. 10 is a schematic view of a mold for insert molding the ring into the esophageal flange;

DETAILED DESCRIPTION OF THE INVENTION

Figure 1:
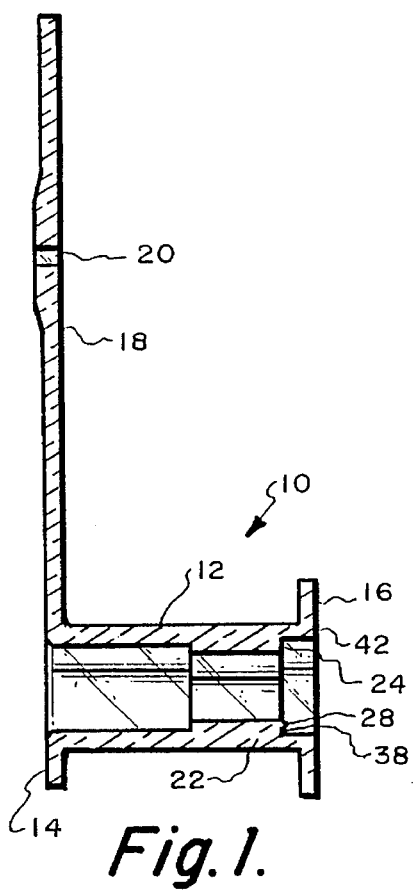
FIG. 1 is a view in section of the body of the voice prosthesis according to the invention.
Figure 2:
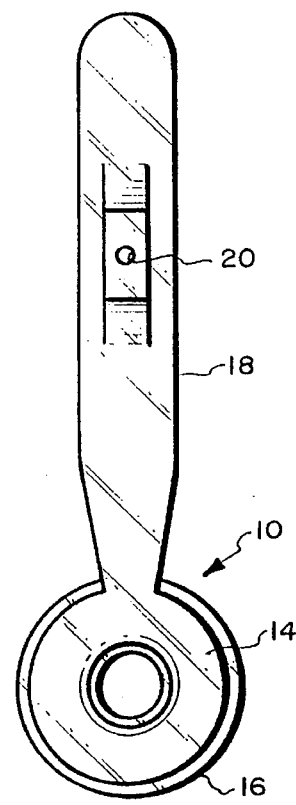
FIG. 2 is a front view in elevation of the body of the prosthesis of FIG. 1.
Figure 3:
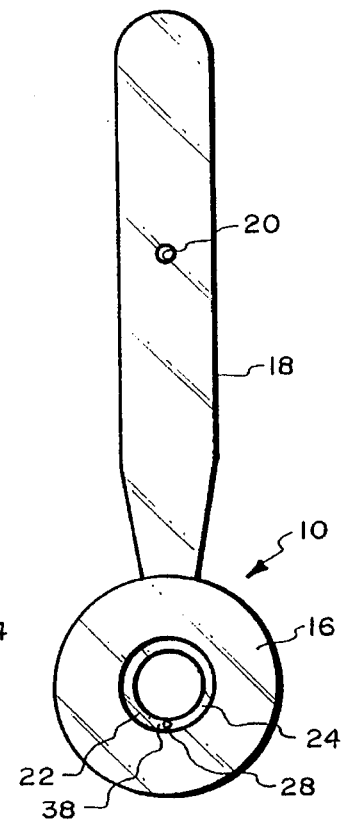
FIG. 3 is a rear view in elevation of the body of the prosthesis of FIG. 1.

Referring now to FIGS. 1–3, a voice prosthesis 10 has a tubular body 12 connected to a front tracheal flange 14 and a rear retention esophageal flange 16. A flexible tab 18 can be attached to the front flange 14. The tab 18 can contain an aperture 20 which can be connected to an insertion tool, not shown. The body 12, first flange 14 and rear flange 16 are preferably a single molded, unitary structure formed from a biocompatible elastomer such as a silicone resin, suitably a 50 durometer, medical grade, silicone elastomer. Since the resin is transparent and the prosthesis structure is small, the prosthesis is difficult to visualize and handle. Therefore, the molding resin generally contains a small amount, from 0.1 to 0.5% of a biocompatible pigment to aid in seeing the device. The pigment can be a heavy metal salt such as barium sulfate.

Figure 4:
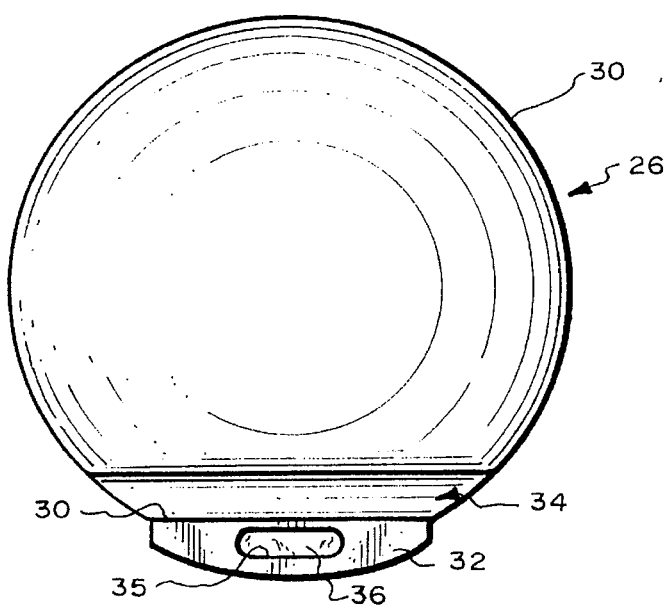
FIG. 4 is a front view in elevation of a valve.
Figure 5:
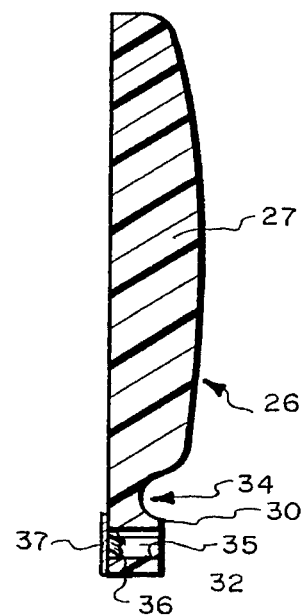
FIG. 5 is a view in section of the valve taken along line 5—5 of FIG. 4.

The cylindrical body can have a thicker rear wall section 22 in which is formed an annular seating ledge 24 for receiving a valve 26 as shown in FIGS. 4–5. The flapper element 27 of the valve 26 is adhesively attached to at least one pin 28 protruding from the ledge 24. In order to increase the reliability of the attachment of the valve for the long-dwelling prosthesis it is preferable to use one larger pin 28 rather than two smaller pins as previously used. Furthermore, the rear flange 16 is made thicker to assure retention of the prosthesis in the fistula. The thickness of the collar is from 0.020 to 0.06 inches, usually about 0.038 inches compared to about 0.020 to 0.030 inches for the standard low-pressure voice prosthesis.

Referring now to FIGS. 4 and 5, the flapper element 27 has a round segment 30 connected to an attachment flap 32. A live hinge 34 in the form of a score line separates the segment 30 from the flap 32. An aperture 35 is provided in the flap 32 for receiving the pin 28. Adhesive 36 forms a film 37 behind the flap and the excess adhesive fills the aperture 34 for adhering the flap 32 to the opposing face 38 of the seating ledge 24.

The prosthesis 10 is transparent to X-rays even through it may contain a low level of a radiopaque pigment such as barium sulfate. If the amount of pigment is increased until the complete prosthesis is radiopaque, it would be difficult to determine if the rear flange was fully seated since the fold could be disposed in front or in back of the body of the prosthesis during X-ray imaging. The fold may not be seen if there is insufficient contrast in grey scale between the rear flange and the rest of the device.

It was then decided to adhere a narrow, opaque ring 40 to the outer face 42 of the rear flange 16 as shown in FIG. 67. The ring has a width at least 10% the diameter of the rear flange usually from 10% to 50% the diameter of the annular rear flange. Usually the rear flange has a diameter of about 0.5 inch and the ring has a width of about 0.05 to 0.10 inch. The ring 40 preferably has an outer perimeter coincident with that of the rear flange 16 so that folds anywhere on the rear flange will be detected by the displayed image of the ring 40. The ring is preferably formed of the same flexible resin as the rear flange but contains an amount of radiopaque pigment such as barium sulfate sufficient to render the ring opaque to X-rays.

Usually the pigment is present in an amount from at least 5% to 35%, generally around 20% by weight. As shown in FIG. 7, the radiopaque ring 40 is adhered to the rear flange with a thin layer 44 of adhesive, such as a medical grade RTV (room temperature vulcanized) silicone adhesive.

The prosthesis of FIGS. 6–7 was readily visualized by X-ray when installed in the fistula of a patient. However, the adhesive film 44 may fail and the ring could fall into the stomach of a patient. Furthermore, it is difficult to maintain the soft pliable ring in circular form when placing it on the adhesive film. It was then decided to place the ring in the cavity for molding the prosthesis and to mold the ring into the rear flange of the prosthesis.

Referring now to FIGS. 8–10 the in-situ molded ring 50 has a thickness of at from 10–100% of the thickness of the rear flange. The ring 50 is placed in the bottom 52 of the cavity 54 of a 2-part mold for molding the prosthesis. The prosthesis or rings can be molded by compression, transfer or injection molding. When the molding resin 56 is injected into the cavity 54, the resin can flow around the ring 50 and can 35 encapsulate and incorporate the ring 50 into the rear flange 16. The resin can be cured by heat, ultraviolet light or moisture. Preferably, the resin cures by heat and pressure during molding. In order to increase the bond between the ring 50 and the rear flange 16, the ring may contain protrusions or tabs 58 disposed on its top and/or bottom surfaces, preferably disposed along its inner edge.

Figure 11:
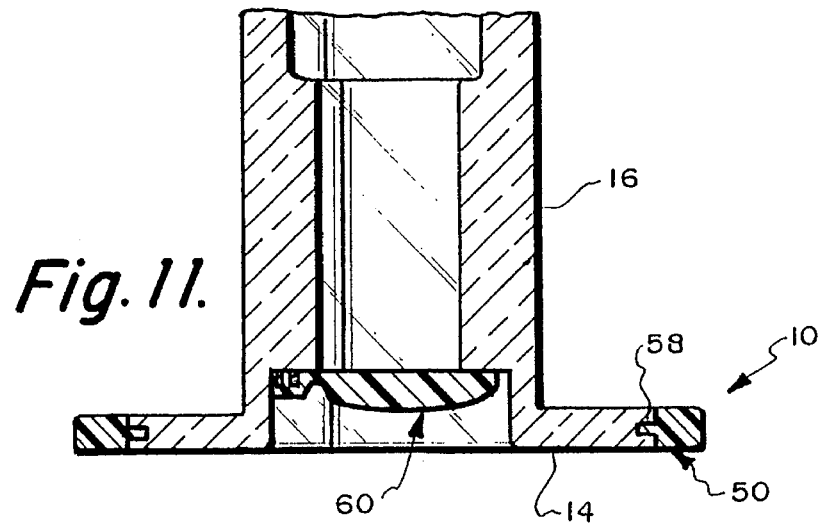
FIG. 11 is a partial view in section of the voice prosthesis with ring and valve assembled in accordance with the invention.
Figure 12:
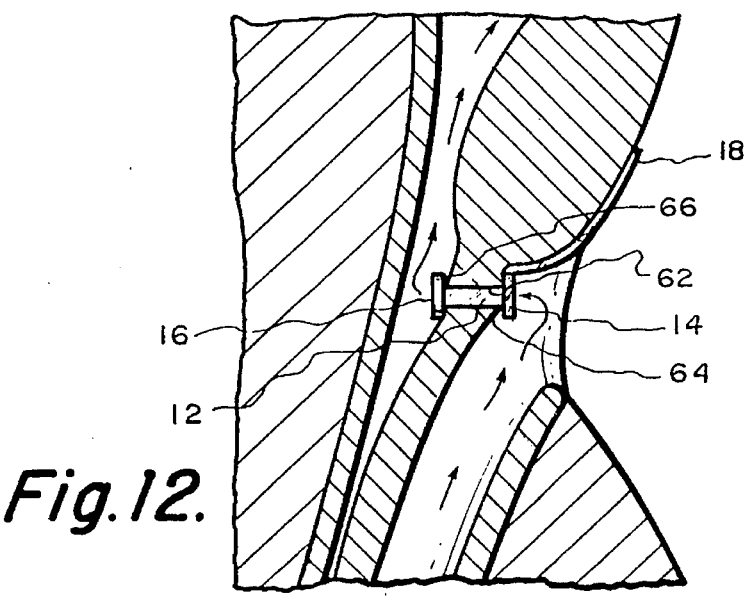
FIG. 12 is a view of the prosthesis installed in a tracheoesophageal fistula.
Figure 13:
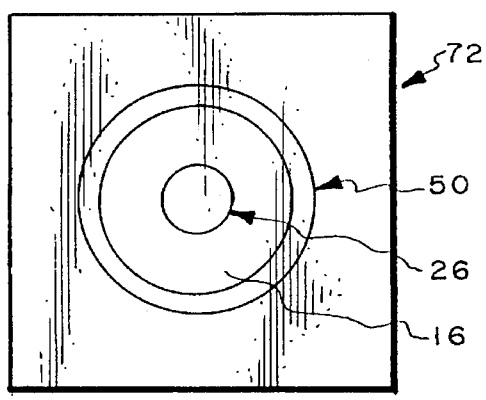
FIG. 13 is a radiographic print of the prosthesis of FIG. 11 with the esophageal flange fully extended.
Figure 14:
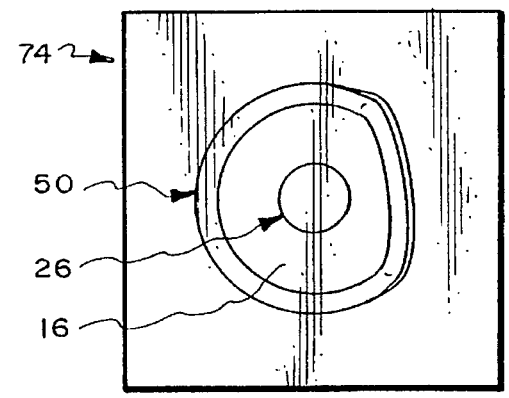
FIG. 14 is a radiographic print of the prosthesis of FIG. 11 installed with the esophageal flange folded.

Referring now to FIG. 11 the prosthesis 10 with in-situ molded ring 50 is shown assembled with a radiopaque valve 60. When the prosthesis is inserted correctly into a fistula 62 as shown in FIG. 12, the front flange 14 of the prosthesis engages the outer wall 64 of the trachea and the rear flange 16 engages the wall 66 of esophagus. The body 12 of the prosthesis prevents the fistula from closing. When the prosthesis is visualized by X-ray, the concentric pattern 72 of the valve 26 and ring 50 as shown in FIG. 13, is indicative of correct deployment of the rear flange. When the X-ray image pattern 74 shows the ring 50 is not a complete circle concentric with the valve 26, it is indicative that the rear flange 16 is folded as shown FIG. 14. The folded outer ring 50 is readily apparent when its image is compared to the image of the circular valve.

EXAMPLE 1

Long dwelling voice prostheses were manufactured by compression and transfer molding from a heat and pressure curable, medical grade, 50 Durometer, silicone elastomer containing 20% $BaSO_4$.

EXAMPLE 2

Clear, long dwelling voice prostheses were molded from the elastomer utilized in Example 1 by transfer and compression molding.

EXAMPLE 3

Rings were compression molded from a medical grade, 50 Durometer, silicone elastomer utilized in Example 1, containing 20% $BaSO_4$ having the following dimensions:

| Sample | Thickness, inches | Outer Diameter, inches |
| --- | --- | --- |
| A | 0.012 | 0.026 |
| B | 0.018 | 0.039 |
| C | 0.021 | 0.054 |

EXAMPLE 4

The rings A, B and C of Example 3 were adhered to the rear flanges of three clear voice prosthesis prepared in Example 2 with a film of RTV silicone adhesive. The opaque voice prosthesis of Example 1 and the 3 voice prostheses containing opaque rings were evaluated for pattern recognition under X-ray with the rear flanges of the prostheses in folded and flat disposition. The voice prostheses with opaque rings attached to the rear flanges were much easier to see and recognize the opaque circular image pattern of the ring against a clear background. When opaque round flapper valve elements were added to the prostheses, the pattern recognition of the rings was further improved.

However, the reliability of the adhesive bond is of concern since the adhesive could fail and the ring could fall into the stomach.

EXAMPLE 5

The ring of Example 3A was insert molded into the body of the prosthesis of Example 1. The prosthesis was pulled until the device failed without delamination of the ring. However, the ring was not totally encapsulated. In the next experiment, knobs were added to the top and bottom surfaces of the ring.

EXAMPLE 6

A ring containing 20% $BaSO_4$ in the silicone elastomer utilized in Example 1, having a thickness of 0.027 inches and a diameter of 0.040 inches was compression molded. The knobs on the top surface had a height of 0.003 inches and the knobs on the bottom surface had a height of 0.004 inches.

EXAMPLE 7

An opaque ring was premolded having retainer tabs on the inner surface of the ring. The retention tabs having a thickness of about 0.010 inches and a radius of 0.015 inches were uniformly disposed on the inner edge of a ring having a thickness of 0.033 inches.

The rings of Examples 6 and 7 were insert molded into the voice prosthesis of Example 2. The prosthesis containing the rings of Example 7 had improved adhesion to the rear flange.

The Indwelling Low Pressure Voice Prosthesis of the invention is designed for those persons who are unable or resistant to changing the voice prosthesis every two or three days as was recommended for the non-indwelling, patient-removable Low Pressure Voice Prosthesis. The Indwelling Low Pressure Voice Prosthesis has been specifically designed to maintain the placement of the prosthesis in the tracheoesophageal puncture so that routine changing of the device is not necessary.

The Indwelling Low Pressure Voice Prosthesis is loaded into a gelatin capsule, using a gel cap loading tool. The gel cap provides a smooth, rounded shape to the tip end of the voice prosthesis, thus enabling easier entry into the tracheoesophageal puncture when placed by the clinician.

The prosthesis is placed in the fistula by inserting the strap of the voice prosthesis into the center hole on the top side of the gel cap loading tool and gently pulling the prosthesis down and through this opening until the rear esophageal flange is positioned over this center hole.

The tubular portion of the voice prosthesis is grasped and the prosthesis is very slowly pulled down further, such that the rear flange on the tip of the voice prosthesis begins to fold forward inside the center hole. Over-pulling will cause the voice prosthesis to be pulled completely through the loading device. The gel cap is placed over the center hole in the loading tool and into the groove, such that it is securely in place. A fingertip is placed on the tip of the gel cap while simultaneously pushing the voice prosthesis back up through the center hole and out of the loading device. The prosthesis is pushed gently until the folded, rear flange is fully residing in the gel cap. The pushrod provided with the gel cap loading tool may be used to push the device through from the back.

The gel cap-tipped end of the voice prosthesis is gently grasped and the prosthesis is carefully pulled the rest of the way back up through the loading device. The prosthesis is placed on the inserter, and the strap attached over the safety peg, as shown in U.S. Pat. No. 5,064,433, the disclosure of which is expressly incorporated herein by reference. The position of the gel cap on the tip of the voice prosthesis is inspected to assure that it is securely and fully encapsulating the rear flange.

A light coating of water or water-soluble lubricant (oil-free) is applied to the tip of the gel-capped end of the voice prosthesis and the voice prosthesis is immediately inserted fully into the tracheoesophageal puncture by aligning the tip of the voice prosthesis partially in the puncture with the neck strap oriented upwards. The prosthesis is held in this position of full insertion for at least 3 minutes. This allows time for the gel cap to dissolve and release the retention collar within the esophagus.

If the prosthesis does not insert easily on the first attempt, do not continue to try to insert. Instead, a clean 22 French tracheoesophageal dilator is inserted for a few minutes to dilate the pathway.

The voice prosthesis strap is detached from the safety peg on the inserter. A finger is placed against the strap and the inserter is carefully withdrawn from the prosthesis with a twisting motion. A piece of tape is placed over the voice prosthesis strap against the skin.

The Indwelling Low Pressure Voice Prosthesis of the invention is designed to permit optional detachment of the strap by a physician or trained speech pathologist following confirmation that the rear flange on the prosthesis is fully opened and securely positioned.

The rear flange emerges from the dissolved gel cap and unfurls within the esophageal lumen. Seating of the rear flange against the anterior wall of the esophagus, can be confirmed by rotating the inserted prosthesis within the puncture while it is attached to the inserter. A correctly and securely inserted prosthesis will rotate freely. Rotate the prosthesis repeatedly 360°. Slight resistance may be detected on the first rotation because of residual gelatin that has not completely dissolved. Allow at lest three minutes for the gel cap to dissolve following prosthesis insertion before proceeding with the rotation confirmation procedure. A voice prosthesis that does not rotate freely suggests that the rear flange has not unfurled and seated within the esophageal lumen. Assessment of the position of the rear flange of the prosthesis is recommended for direct confirmation/assessment.

An A-P radiograph of the tracheostoma according to the invention is useful in confirming positioning of the rear flange within the esophageal lumen. The circumferential edge of the rear, esophageal flange on the voice prosthesis is marked with a radiopaque band that forms a perfect circle. If the rear flange has completely unfurled within the esophageal lumen, this "perfect circle" radiopaque marker is visualized as a circle. A deformed circular radiopaque marker indicates that the rear flange has not entered and correctly unfurled within the esophageal lumen. This suggests that the voice prosthesis that has been inserted is either not long enough or has not been fully inserted into the tracheoesophageal puncture such that the rear flange has not entered the esophagus. Further assessment, remeasurement, and reinsertion are necessary. The strap on the voice prosthesis should not be detached until correct position of the rear flange within the esophagus can be confirmed.

It is recommended that the strap not be detached from a voice prosthesis if the clinician anticipates the simultaneous use of a tracheal tube that may potentially dislodge the voice prosthesis.

Removal of the Indwelling Low Pressure Voice Prosthesis should only be done by grasping the outer rim of the device securely with a hemostat. Pull gently and firmly until the prosthesis is fully withdrawn. Insert a 22 French dilator and tape it into position for five minutes prior to inserting a new Indwelling Low Pressure voice Prosthesis that has been attached to an inserter. Never remove one voice prosthesis and reinsert another voice prosthesis without first dilating the tracheoesophageal puncture with the 22 French dilator. Always use a gel cap on the tip of an Indwelling Low Pressure Voice Prosthesis to enable easy, atraumatic insertion.

The Indwelling Voice Prosthesis may be left in place in the tracheoesophageal puncture until it ceases to function correctly, that is, until it leaks or is not providing adequate voice for speech. If the prosthesis is not functioning properly, the patient should return to the clinician for evaluation.

The Blom-Singer Flushing Pipet provides a means for flushing small particulate matter from the lumen and valve member of the Blom-Singer Indwelling Low Pressure Voice Prosthesis while in-situ, i.e., in the user's tracheoesophageal puncture. The following instructions should be made clear to the patient as part of the routine care of the Blom-Singer Indwelling Low Pressure Voice Prosthesis.

The patient should illuminate the tracheostoma with a bright light source such that the open end of the voice prosthesis is clearly visible. Use long handled forceps (tweezers) to carefully remove any dried debris (phlegm) that may be in the open end of the voice prosthesis.

Fill approximately one third of the stem of the pipet with clean water. Carefully and gently insert the tip of the pipet into the voice prosthesis only until it abuts against the stopper on the stem of the pipet. Briskly squeeze the bulb on the pipet to flush a rapid squirt of water through the voice prosthesis. If liquid will not readily squirt through the voice prosthesis, this indicates that it may be plugged with dried phlegm. Allow a few drops of water to dissolve this dried matter for a few minutes and then re-flush with the pipet until the debris breaks free. The debris must be removed from the tracheoesophageal puncture with a hemostat by the clinician for thorough cleaning. Never attempt to reinsert an Indwelling Low Pressure Voice Prosthesis that has the strap removed.

After flushing, remove the pipet carefully to avoid dislodging the voice prosthesis. Inspect the interior of the voice prosthesis with a bright light. Repeat flushing as needed.

If the voice prosthesis is accidently dislodged from the puncture, the patient should be instructed to immediately place a 22 French dilator in the puncture to keep the puncture from closing. The patient should then return to his/her clinician for re-insertion of the voice prosthesis.

It is to be realized that only preferred embodiments of the invention have been described and that numerous substitutions, modifications and alterations are permissible without departing from the spirit and scope of the invention as defined in the following claims.

We claim:

1. A voice prosthesis for insertion into a fistula in a tracheoesophageal wall of a patient comprising in combination:

a hollow, annular, flexible body to be disposed in and to maintain said fistula open, said body having a first tracheal end and a second esophageal end;

a first flange connected to the first end of the body;

a second flange connected to the second end of the body, said second flange being substantially transparent to X-ray radiation;

an element containing sufficient pigment to be opaque when radiated by X-ray radiation said element adhered to said second flange, having a first, distinctive X-ray, image when the second flange is fully seated on said wall and having a second, distinctive X-ray image when the second flange is not fully seated on said wall said second image being substantially different from said first image; and a flapper valve connected to the second end of the body.

2. A voice prosthesis according to claim 1 in which the flapper valve contains sufficient pigment to be opaque when irradiated by X-rays.

3. A voice prosthesis according to claim 1 in which the radiopaque element is adhered to the second flange by molding the element into the second flange.

4. A voice prosthesis according to claim 3 in which protrusions extend from the surface of the element to improve adherence between the element and the second flange.

5. A voice prosthesis according to claim 1 in which the element is in a form of a polygon.

6. A voice prosthesis according to claim 5 in which the element is an annular ring.

7. A voice prosthesis according to claim 6 in which the protrusions extend inwardly from an inner edge of the ring.

8. A voice prosthesis according to claim 1 in which the prosthesis is formed from a flexible, medical grade elastomer.

9. A voice prosthesis according to claim 8 in which the elastomer is a silicone resin.

10. A voice prosthesis according to claim 1 in which said body including said first and second flanges are a monolithic structure containing no more than 3% by weight of an opaque pigment.

11. A voice prosthesis according to claim 10 in which the radiopaque element contains at least 5% by weight of a heavy metal salt.

\* \* \* \* \*